United States Patent [19]
Weldon et al.

[11] Patent Number: 5,080,110
[45] Date of Patent: Jan. 14, 1992

[54] PACIFIER EAR PLUGS

[76] Inventors: Patrizia M. Weldon; Jeffrey L. Weldon, both of San Diego County, Calif.

[21] Appl. No.: 594,335

[22] Filed: Oct. 9, 1990

[51] Int. Cl.⁵ .............................................. A61F 11/00
[52] U.S. Cl. ..................................... 128/864; 606/234
[58] Field of Search ............................... 128/864–867; 606/234–236; 2/209, 174, 243 R

[56] References Cited

U.S. PATENT DOCUMENTS

| | | | |
|---|---|---|---|
| 1,344,935 | 6/1920 | Baum | 128/864 |
| 2,230,738 | 2/1941 | Baum | 128/864 |
| 2,538,339 | 1/1951 | Thomas | 128/864 |
| 2,824,561 | 2/1958 | Mueller | 606/234 |
| 3,267,937 | 8/1966 | Verschoor | 606/236 |
| 3,455,292 | 7/1969 | Mudrinich | 606/236 |
| 3,610,248 | 10/1971 | Davidson | 606/236 |
| 4,143,452 | 3/1979 | Hakim | 606/236 |
| 4,195,638 | 4/1980 | Duckstein | 606/236 |
| 4,554,919 | 11/1985 | Hubert | 606/234 |

FOREIGN PATENT DOCUMENTS 2100606  1/1983  United Kingdom ................ 128/864

*Primary Examiner*—Robert A. Hafer
*Assistant Examiner*—Michael Brown
*Attorney, Agent, or Firm*—Ralph S. Branscomb

[57] ABSTRACT

The invention is an external ring, a radial collar, and a protruding portion which extends inside the ear canal to dampen sound. In the preferred embodiment, the collar and the exterior of the protruding portion are molded of a soft, flexible rubber, and the ring is made of a rigid plastic and includes an extending cylindrical core which inserts into the protrusion to make the two parts integral. The ear plug has a dual function, first, to conveniently permit insertion of the plug into the ear to the proper depth automatically and to prevent its easy removal, and secondly, to imitate as exactly as possible a scaled down version of a baby pacifier to enhance the ability to sell a pair of the units as novelty items.

3 Claims, 1 Drawing Sheet

PACIFIER EAR PLUGS

BACKGROUND OF THE INVENTION

Anyone who has had children will remember the early days in their lives when the cumulative impact of their crying drove parents to distraction. Most parents wished they could simply use ear plugs to get a little peace and quiet, but were prevented from doing so by their image of themselves as good parents.

The level of annoyance caused by the sound increases is in direct relationship to the background sound environment. For example, a level of 30 dB over the background environment noise level will ordinarily be experienced as annoying.

Anyone who has heard a baby or a small child scream, cry or shriek would agree that this sound is annoying. Typically, this sound exceeds 30 dB over background, and is of a pitch and tone to be truly annoying. Such irritation can cause fatigue, nervousness and hypertension, and adds to the overall stress that the parent feels anyway. Efficiency is reduced, balance is upset, and blood vessels constrict.

Additionally, people who have used ear plugs sometimes worry that they may insert the ear plugs too far into the ear and possibly damage the ear, or that they may not be able to retrieve the ear plugs once they are in place.

These two facts dove tail into the creation of the instant invention.

SUMMARY OF THE INVENTION

The instant invention is derived from the above two problems and comprises an ear plug that resembles a scaled down version of a baby pacifier. As indicated above, the purpose of the ear plug is dual in nature. First, on a purely functional level, the pacifier shape of an earplug coincides exactly with the shape needed to prevent the earplug from being inserted too far into the ear, and with the ability to easily remove the ear plug by pulling a ring typical of a ring on a pacifier. The same considerations dictate the design of a pacifier. The invention is actually a pacifier for the parents.

Secondly however, and more importantly from a commercial and marketing perspective, is the deliberate creation of the ear plug to resemble a pacifier, so that it may be sold (in pairs, of course) through outlets which merchandise infant products to parents. Although the ear plugs are quite functional and work well, they would ordinarily be sold to be used as light hearted gifts, inasmuch as most parents are still going to be reluctant to use ear plugs to avoid hearing the baby's crying.

DETAILED DESCRIPTION OF THE PREFERRED EMBODIMENT

Figure 1:
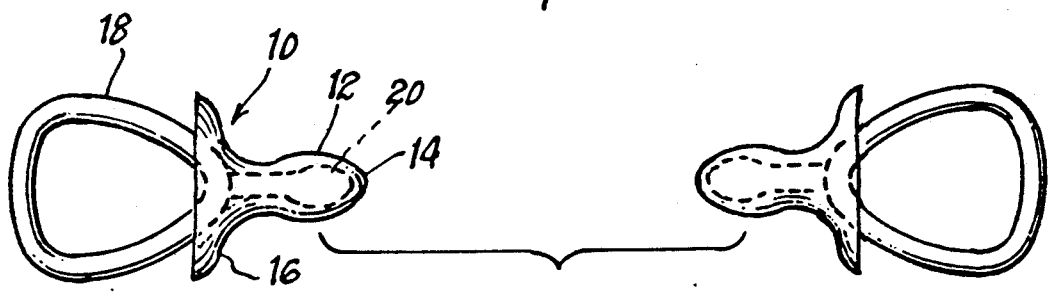
FIG. 1 illustrates a pair of the ear plugs in a posed relation and in side elevation.
Figure 2:
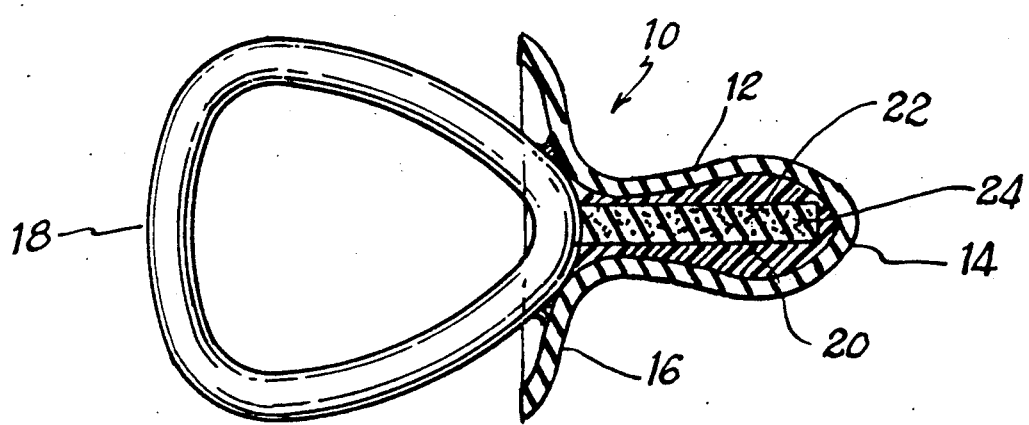
FIG. 2 illustrates in detail the construction of an ear plug with portions in section; and, FIG. 3 illustrates the ear plugs in use by a distraught parent.
Figure 3:
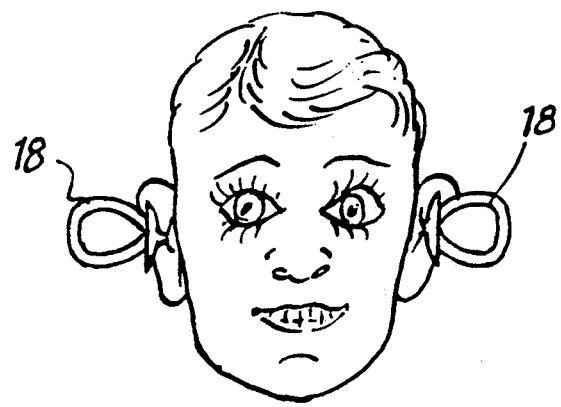

Although there are a number if ways of making the unit so that it resembles a pacifier, in the preferred embodiment, it is made in two parts. The first part comprises a soft, flexible unit 10 comprising a tubular outer sheathing 12 which passes into the ear terminating in a closed tip 14, and a flared radial collar 16 at the other end from the tip. This piece is very economically molded in a material that is either rubber or a simulated rubber.

The second piece comprises a rigid ring 18 that is connected to the flexible unit 10. In the preferred embodiment, this connection is made by means of a cylindrical plug 20 which preferably has an annular boss 22 at the inside end to more positively engage the enlarged tip end of the flexible unit 10. The plug 20 may be filled with sound absorbing foam material 24.

As stated, there are clearly different ways of creating the same effect. The basis of the invention is that the ear plug resemble a pacifier, incorporating the ring 18, the collar 16, and the portion 12 that extends into the ear resembling the portions of the pacifier that is inserted into the mouth. Conceivably this entire structure could be made by a single molding. If the unit is designed purely as a gag item, obviously it could be made more simply and would not need the sound absorbing qualities, or the soft flexibility of the portion that is inserted into the ear.

In any event, the unit should closely resemble a pacifier in appearance, and in no event should be unsafe should it actually be used as an ear plug. In the preferred embodiment, it is actually an ear plug, and would represent probably the easiest ear plug to use on the market.

It is hereby claimed:
1. An ear plug comprising:
   (a) a ring;
   (b) a protrusion attached to said ring for insertion into the ear;
   (c) a radial collar surrounding said protrusion substantially at its juncture with said ring;
   (d) said protrusion comprising a tubular outer sheathing and an inner plug; and
   (e) said inner plug including a mass of sound-absorbing material.
2. An earplug is comprising:
   (a) a ring
   (b) a protrusion attached to said ring for insertion into the ear, comprising a tubular outer sheathing and an inner plug;
   (c) a radial collar surrounding said protrusion substantially at its juncture with said ring and defining a unitary flexible unit with said collar;
   (d) said ring and inner plug defining an integral unit attached to said flexible unit by virtue of the insertion of said plug into said tubular outer sheathing; and
   (e) said plug comprising a hollow outer cylinder molded as an integral part of said ring and a sound-absorbing foam mass filling said cylinder.
3. Structure according to claim 2 wherein said ear plug is shaped and proportioned to resemble a scaled down baby pacifier.